(12) United States Patent
Fugo (10) Patent No.: US 7,959,632 B2
(45) Date of Patent: Jun. 14, 2011

(54) PLASMA INCISING DEVICE INCLUDING DISPOSABLE INCISING TIPS FOR PERFORMING SURGICAL PROCEDURES

(76) Inventor: Richard J. Fugo, Plymouth Meeting, PA (US)

(*) Notice: Subject to any disclaimer, the term of this patent is extended or adjusted under 35 U.S.C. 154(b) by 1182 days.

(21) Appl. No.: 11/584,657

(22) Filed: Oct. 20, 2006

(65) Prior Publication Data

US 2007/0093868 A1 Apr. 26, 2007

Related U.S. Application Data

(60) Provisional application No. 60/728,445, filed on Oct. 20, 2005.

(51) Int. Cl.
*A61B 18/18* (2006.01)
(52) U.S. Cl. .......................................... 606/45; 606/41
(58) Field of Classification Search ............... 606/45–47
See application file for complete search history.

(56) References Cited

U.S. PATENT DOCUMENTS

| | | | | |
|---|---|---|---|---|
| 2,110,735 A | * | 3/1938 | Marton | 606/44 |
| 4,901,719 A | * | 2/1990 | Trenconsky et al. | 606/49 |
| 5,195,959 A | * | 3/1993 | Smith | 604/34 |
| 5,693,044 A | * | 12/1997 | Cosmescu | 606/42 |
| 5,958,266 A | | 9/1999 | Fugo et al. | 219/151.29 |
| 6,086,585 A | * | 7/2000 | Hovda et al. | 606/45 |
| 6,213,999 B1 | * | 4/2001 | Platt et al. | 606/27 |
| 6,479,785 B1 | | 11/2002 | Rothe et al. | 435/194 |
| 6,787,730 B2 | | 9/2004 | Coccio et al. | 219/121.44 |
| 6,867,387 B2 | | 3/2005 | Fugo et al. | 219/121.44 |
| 2002/0111608 A1 | * | 8/2002 | Baerveldt et al. | 606/6 |
| 2003/0225401 A1 | * | 12/2003 | Eggers et al. | 606/39 |
| 2004/0030330 A1 | * | 2/2004 | Brassell et al. | 606/41 |
| 2004/0044342 A1 | * | 3/2004 | Mackay | 606/45 |
| 2004/0186470 A1 | * | 9/2004 | Goble et al. | 606/41 |
| 2004/0236325 A1 | * | 11/2004 | Tetzlaff et al. | 606/51 |
| 2006/0041257 A1 | * | 2/2006 | Sartor et al. | 606/42 |

* cited by examiner

*Primary Examiner* — Linda C Dvorak
*Assistant Examiner* — Jaymi Della (57) ABSTRACT

An apparatus for performing surgery using plasma is described. The apparatus includes a plasma generating unit, a plasma wand and a foot pedal. The plasma wand further includes a disposable tip which may be removed and replaced for each surgical procedure, so as to maintain operating sterility.

6 Claims, 7 Drawing Sheets

PLASMA INCISING DEVICE INCLUDING DISPOSABLE INCISING TIPS FOR PERFORMING SURGICAL PROCEDURES

RELATED APPLICATIONS

This is a non-provisional application based on provisional application U.S. Ser. No. 60/728,445 to Richard J. Fugo, filed Oct. 20, 2005.

FIELD OF THE INVENTION

This present invention relates to an apparatus for performing surgical procedures using plasma, and in particular, to a plasma incising surgical unit and disposable tips for use in surgical procedures.

BACKGROUND OF THE INVENTION

U.S. Pat. Nos. 5,958,266, 6,479,785, 6,787,730 and 6,867,387 describe methods and apparatus for incising tissue using plasma, and their separate disclosures are hereby incorporated by reference into the present application. These patents disclose how to generate and maintain plasma without using a traditional gas or liquid fuel (e.g., Argon). Instead, these patents disclose how to generate and maintain plasma using atomic particles which surround the point of incision. Several of the patents describe a handpiece 26 with an incising electrode tip 28. In operation, the handpiece is grasped by the user (i.e., surgeon), and the incising electrode tip 28 is used to create an incision in tissue.

However, the above-reference patents do not disclose specific methods for maintaining sterility in an operating environment, such as for example, through the use of disposable operating members.

Thus, there is presently a need for an apparatus which permits the simple and efficient incision of tissue using plasma, but which also maintains operating sterility.

SUMMARY OF THE INVENTION

An exemplary embodiment of the present invention comprises an apparatus including a plasma generating unit and a plasma wand coupled to the plasma generating unit, the plasma wand further including a first removable tip.

An exemplary embodiment of the present invention also comprises a disposable tip for use in plasma surgery including a main body and a filament extending from one end of the main body, the filament being partially enclosed within an insulating sheath.

An exemplary embodiment of the present invention also comprises a method for making a disposable tip for use in plasma surgery, including the steps of disposing a filament within a first housing, applying a first insulating sheath around a first portion of the filament, bending the first portion of the filament at a predetermined angle with respect to a principal axis of the filament.

An exemplary embodiment of the present invention also comprises a method for performing a sclerostomy procedure using plasma, including the steps of inserting a first plasma incising tip into a plasma wand, the plasma wand being coupled to a plasma generating unit, performing a transscleral procedure, removing the first plasma incising tip from the plasma wand, inserting a second plasma incising tip into the plasma wand, and performing a transciliary procedure.

DETAILED DESCRIPTION

Figure 1:
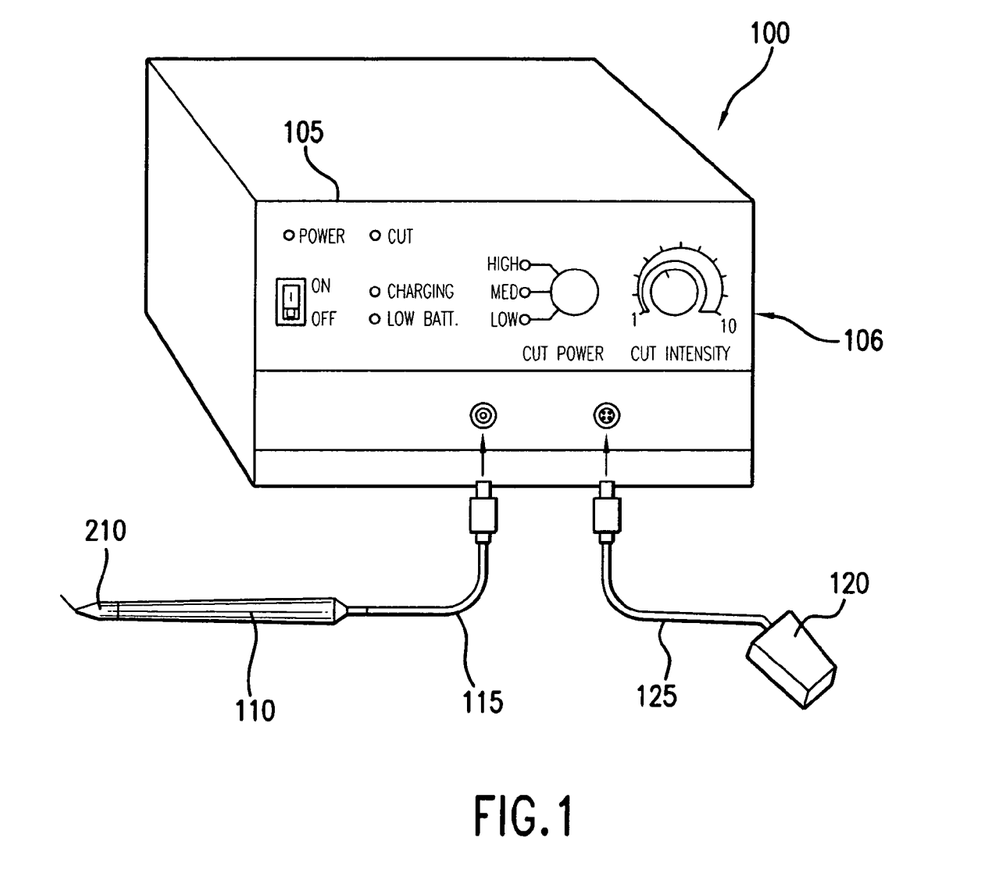
FIG. 1 shows a front view of a plasma incising system according to an exemplary embodiment of the present invention.

FIG. 1 shows a plasma incising system 100 according to an exemplary embodiment of the present invention. The system 100 includes a plasma generating unit 105, and a plasma wand 110 which may be coupled to the plasma generating unit 105 by a first electrical connection means 115 (e.g., electrical cord). The system 100 also includes a foot pedal 120 which may be coupled to the plasma generating unit 105 by a second electrical connection means 125 (e.g., electrical cord). Although the first and second electrical connection means 115, 125 are shown disconnected from the plasma generating unit 105 in FIG. 1, those of ordinary skill in the art will realize that these connection means must be coupled to the plasma generating unit (at the ports shown) in order for the system 100 to operate. When depressed by the surgeon, the foot pedal 120 activates the plasma generating unit 105, and accordingly sends an electrical signal to the plasma wand 110 which creates plasma for performing surgery. In one exemplary embodiment, the foot pedal 120 may be provided with an additional activation lever 121 (not shown). The activation lever 121 must be pressed forward prior to depressing the foot pedal 120, and thus prevents the accidental activation of the plasma generating unit 105.

Figure 2A:
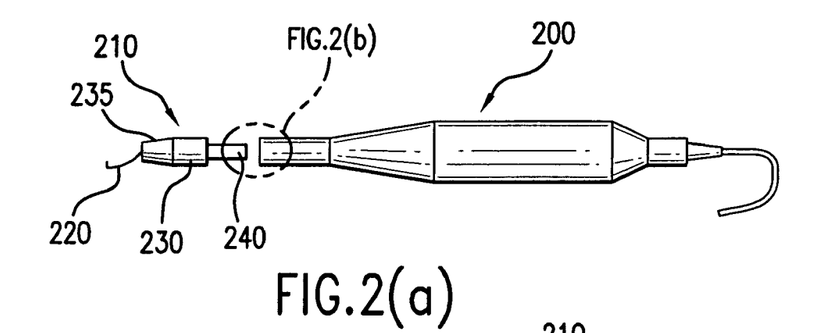
FIG. 2(a) shows an exploded view of a plasma wand according to an exemplary embodiment of the present invention.
Figure 2B:
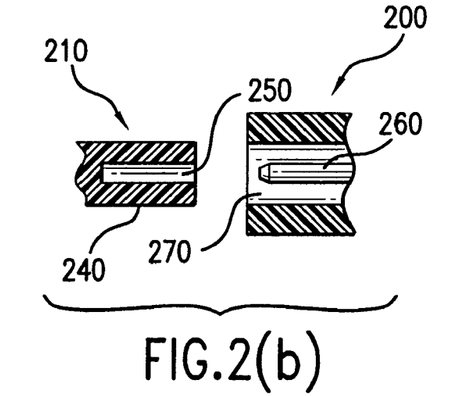
FIG. 2(b) shows a detail view of the plasma wand of FIG. 2(a).

In one preferred embodiment of the invention, the plasma generating unit 105 comprises a rechargeable, battery powered, unit. Further, although the first and second electrical connection means are shown as electrical wires in FIG. 2, this of ordinary skill in the art will note that the first and second electrical connection means 115, 125 may comprise one or more wireless connections (e.g., radiofrequency, infrared, BlueTooth™, etc.) between the plasma generating unit 105, and the respective plasma wand 110 and foot pedal 120.

As shown in detail in FIG. 2, the plasma wand 110 includes a main body 200, and a disposable tip 210. In order to maintain operating sterility, one disposable tip 210 is preferably used for each operation performed using the plasma system 100, and in some exemplary embodiments, different disposable tips are used for different phases of complex operations. The disposable tip 210 further includes a filament 220 which is disposed a particular angle with respect to the principal axis of the remainder of the tip. The disposable tip 210 also includes a main body 230 which has a frustoconical first end 235 and a cylindrical second end 240. As shown in detail in FIG. 2(b), the second end 240 of the disposable tip 210 includes a conical recess 250 (i.e., female contact) for receiving a conical connector pin 260 disposed within the main body 200. The main body 200 also includes a conical recess 270 for receiving the second end 240 of the disposable tip 210. The first end 235 of the disposable tip main body 230 is coupled to the filament 220 through a "friction fit" as described in more detail with reference to FIGS. 6-9 below.

Figure 2C:
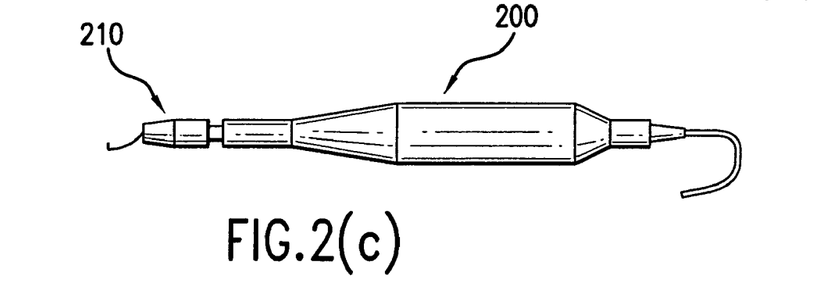
FIG. 2(c) shows the plasma wand of FIG. 2(a) with a disposable tip partially inserted therein.
Figure 2D:
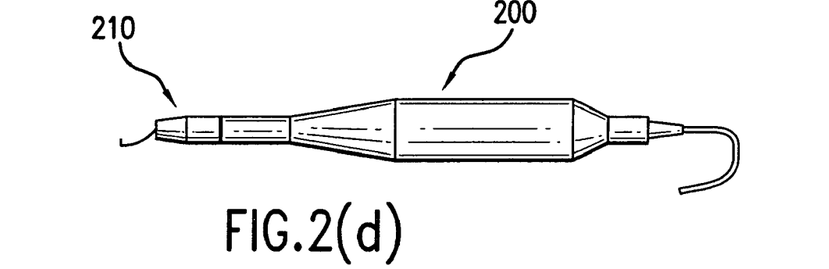
FIG. 2(d) shows the plasma wand of FIG. 2(a) with a disposable tip fully inserted therein.
Figure 3:
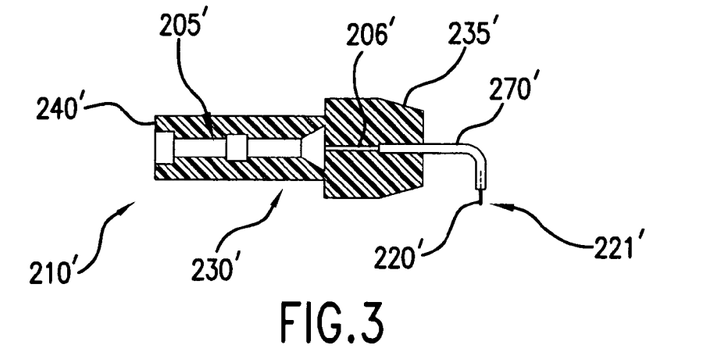
FIG. 3 shows a cross-sectional view of a disposable tip according to a first exemplary embodiment of the present invention.
Figure 4:
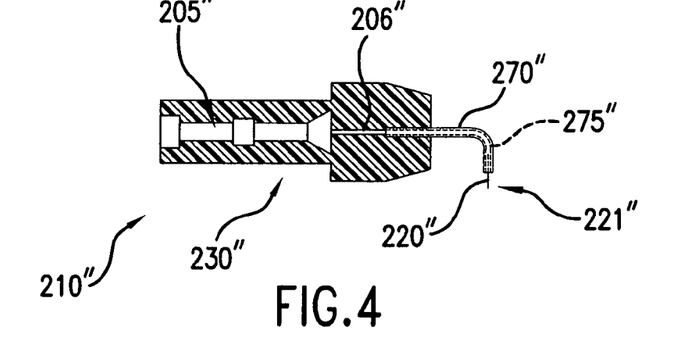
FIG. 4 shows a cross-sectional view of a disposable tip according to a second exemplary embodiment of the present invention.
Figure 5:
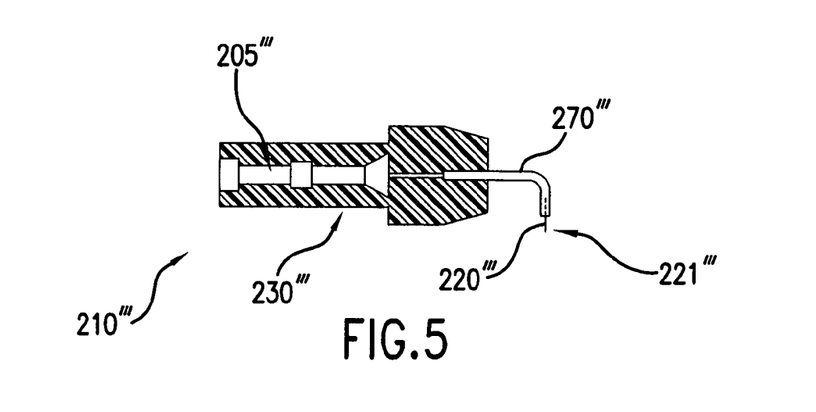
FIG. 5 shows a cross-sectional view of a disposable tip according to a third exemplary embodiment of the present invention.

As noted above, a portion of the filament 220 is preferably disposed at an angle with respect to a principal axis of the main body 230 of the disposable tip 210 (e.g., 90), as shown in more detail in FIGS. 3-5. In an exemplary embodiment of the present invention, there exists a 'friction fit' between the disposable tip 210 and the main body 200, such that the disposable tip is retained within the main body once fully inserted (See FIGS. 2(c) [partial insertion] and 2(d) [full insertion]). The disposable tip 210 is intended for single use only; after a single use, the disposable tip 210 should be discarded according to proper guidelines for biomedical waste.

The disposable tip 210 may come in various configurations depending upon the surgical procedure to be performed. For example, for a sclerostomy procedure, there may be separate disposable tips for the transscleral and transciliary portions of the procedure. In one exemplary embodiment according to the present invention, a disposable tip 210' for a transscleral procedure includes a stainless steel filament 220' which extends approximately 0.5 millimeters (mm) beyond a sheath 270' of insulating material (e.g., Teflon®), and is approximately 0.6 mm in diameter (See FIG. 3). In another exemplary embodiment according to the present invention, a disposable tip 210" for a transciliary procedure includes a stainless steel filament 220" which extends approximately 0.75 mm beyond a sheath 270", and is approximately one hundred (100) microns in diameter (See FIG. 4). In another exemplary embodiment according to the present invention, a disposable tip 210''' for a transciliary procedure includes a stainless steel filament 220''' which extends approximately 0.75 mm beyond a sheath 270''', and is approximately three hundred (300) microns in diameter (See FIG. 5).

FIGS. 3-5 show various embodiments of disposable tips 210 which may be used for different types of surgical procedures.

FIG. 3 shows a disposable tip 210' which includes a main body 230' with a first frustoconical end 235' and a second conical end 240'. A filament 220' protrudes from the second end 240', and is partially surrounded by an insulating sheath 270'. A first portion 221' of the filament 220' protrudes beyond the sheath 270'. As described in more detail below with reference to FIGS. 6-9, the main body 230 is comprised of mating male and female members. A wire crimp device 205' is disposed within the main body 230' and is held in place by the male and female members. The wire crimp device 205' holds the filament 220', as shown and described in detail below with reference to FIG. 10. The main body 230' also includes a filament channel 206' through which the filament 220' extends. In one exemplary embodiment, the filament 220' has a diameter of approximately 0.6 mm (600 microns). Because the filament 220' is inserted directly into the tissue during surgery, those of ordinary skill in the art will realize that the diameter of the filament directly affects the size of the incision. The disposable tip 210' is preferably used in the transscleral portion of a sclerostomy procedure, but may be used for any type of surgical procedure where it is deemed appropriate by one of ordinary skill in the art.

FIG. 4 shows a disposable tip 210" with similar features to disposable tip 210' discussed above, and similar part numbers designate similar elements. The key difference in design is that the presence of an additional internal insulating sheath 275". In particular, the disposable tip 210" contains an internal insulating sheath 275" which is disposed within an (external) insulating sheath 270". The insulating sheathes 270", 275" are of differing thicknesses, such that the (external) insulating sheath 270" is thicker than the internal insulating sheath 275". Such a construction for the disposable tip 210" allows deep, thin ablation of tissue with little or no obstruction of the ablation site (i.e., the user can see what he or she is cutting more clearly). Another difference between disposable tip 210" and disposable tip 210' is the thickness (i.e., diameter) of the filament 220". Whereas the filament 220' in the disposable tip 210' is preferably larger in size (e.g., 600 microns), in one exemplary embodiment, the filament 220" has a diameter of approximately 0.1 mm (100 microns). The disposable tip 210" is preferably used in the transciliary portion of a sclerostomy procedure, but may be used for any type of surgical procedure where it is deemed appropriate by one of ordinary skill in the art.

FIG. 5 shows a disposable tip 210''' with similar features to disposable tip 210' discussed above, and similar part numbers designate similar elements. The key difference is that the filament 220''' is of a different thickness (i.e., diameter) from the filament 220' described above with reference to disposable tip 210'. In some cases, it may be advantageous to ablate a pit (e.g., scleral pit) first with a tip of a first (e.g., larger) diameter (such as tip 210' discussed above), and thereafter perform subsequent ablation using a tip with a second (e.g., smaller) diameter (such as tip 210'''). However, such decisions are dependent upon the clinical presentation of the surgical site, and the structure of the tissue being operated upon (e.g., the structure of the eye). In one exemplary embodiment, the filament 220''' has a diameter of approximately 0.3 mm (300 microns). The disposable tip 210''' is preferably used in the transciliary portion of a sclerostomy procedure, but may be used for any type of surgical procedure where it is deemed appropriate by one of ordinary skill in the art.

In addition to the procedures mentioned above, the exemplary disposable tips 210', 210'' and 210''' are appropriate to create precise ostomy openings through the sclera and into the anterior chamber of the eye. These exemplary disposable tips are also appropriate to create precise ostomy openings through the sclera, through the cornea, and into the anterior chamber of the eye. Moreover, plasma ablation has been shown to produce minimal trauma on the (scleral or corneal) ablation pit tissue wall.

In one exemplary embodiment, the plasma generating unit 105 comprises a metal enclosure measuring approximately six (6) inches (15.2 cm) high by ten (10) inches (25.4 cm) wide by seven (7) inches (17.8 cm) deep. Components to be used by operating room personnel are located on front panel 106 and back panel 107 (not shown) of the plasma generating unit 105. The back panel 107 (not shown) of the plasma generating unit 105 has only one user component with an electrical connector labeled "CHARGER". This electrical connector accepts the mating electrical connector from the Alternating Current (AC) Battery Charger provided with the system 100. The AC Battery Charger accepts a standard 120/240 Volts AC (VAC), 50/60 Hertz (Hz) outlet. All other components and controls are located on the front panel 106 of the plasma generating unit 105. A display of the front panel 106 of the plasma generating unit 105 is shown in FIG. 1 of the present application, and is described below.

FIG. 1 shows the front panel 106 of the plasma generating unit 105 in detail. The front panel 106 includes various controls, including: (a) an ON-OFF Switch, (b) a Power Indicator Light, (c) a "CUT" Indicator Light (Yellow), (d) a "CHARGING" Indicator Light, (e) a "LOW BATT" Indicator Light, (f) a "CUT POWER" Switch, (g) a "CUT INTENSITY" Dial, (h) a "HANDPIECE" Connector, and (i) a "FOOT SWITCH" Connector. The ON-OFF Switch must be placed in the "ON" position in order to operate the system 100. The ON-OFF Switch should be placed in the "OFF" position when the system 100 is not in use for an extended period of time. The plasma generating unit 105 is automatically disconnected from the AC Battery Charger when the ON-OFF Switch is on the "ON" position. When the plasma generating unit 105 is connected to the AC Battery Charger, the plasma generating unit 105 is operating only on battery power, therefore, the plasma generating unit 105 cannot have its batteries charged while the ON-OFF Switch is in the "ON" position. The Power Indicator Light is only lit when the plasma generating unit 105 is energized, the "ON-OFF" Switch is in the "ON" position, and the internal rechargeable batteries of the unit are sufficiently charged. The "CUT" Indicator Light is only lit when the plasma generating unit 105 is activated, and the foot pedal 120 is depressed. In one preferred embodiment, an audible tone will be heard from the plasma generating unit 105 when it is in "CUT" mode. The "CHARGING" Indicator Light is only lit when the plasma generating unit 105 is being charged by the AC Battery Charger. As noted above, the plasma generating unit 105 will not charge while the ON-OFF Switch is in the "ON" position. When the ON-OFF Switch is in the "ON" position, the plasma generating unit 105 is automatically isolated from the AC Battery Charger for added patient safety. The "LOW BATT" Indicator Light is only lit when the internal rechargeable batteries need to be recharged by the AC Battery Charger. The plasma generating unit 105 should still continue to cut for a minimum of (4) four minutes once this indicator becomes lit, however, it is recommended to always have a sufficient charge prior to performing operations using the system 100. The "CUT POWER" Switch has three positions: high, medium and low. This switch refines the cutting power of the disposable incising tip 210. The "CUT INTENSITY" Dial is continuously variable from position one (lowest) through position ten (highest). This dial varies the cutting intensity on the disposable incising tip 210. The "HANDPIECE" Connector comprises a female electronic connector that is designed to accept a male electronic connector disposed at one end of the first electrical connection means 115. The "FOOT SWITCH" Connector comprises a female electronic connector which is designed to accept a male electrical connector disposed at one end of the second electrical connection means 125.

Figures 6, 7, 8, 9:
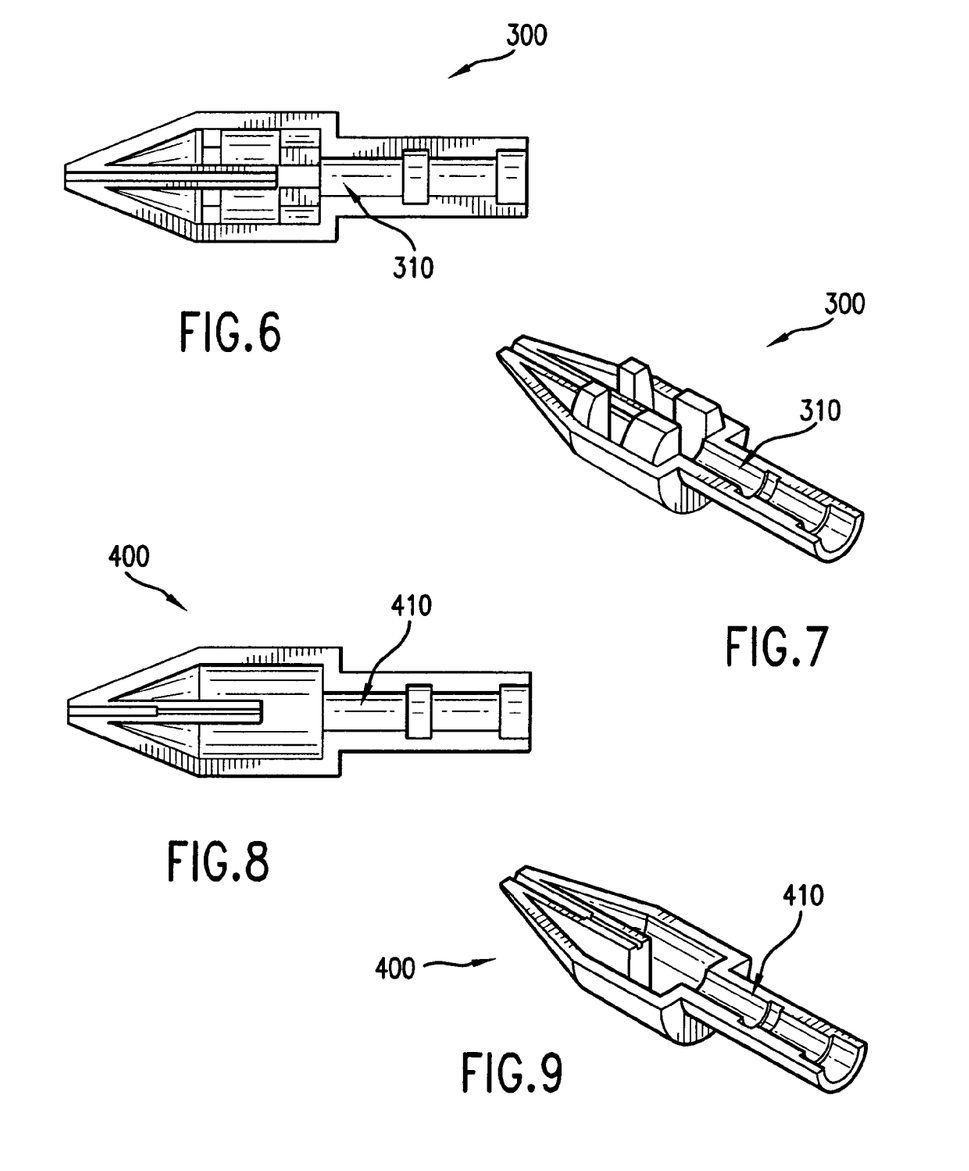
FIG. 6 shows a top view of a male portion of a disposable tip main body according to an exemplary embodiment of the present invention.
FIG. 7 shows a top perspective view of the male portion of the disposable tip main body shown in FIG. 6.
FIG. 8 shows a top view of a female portion of a disposable tip main body according to an exemplary embodiment of the present invention.
FIG. 9 shows a top perspective view of the female portion of the disposable tip main body shown in FIG. 8.

FIGS. 6-9 show additional details of the disposable tip 210. The disposable tip main body 230 is comprised of two (2) separate members which interlock with one another. FIG. 6 shows a top view of the male member 300, and FIG. 7 shows a perspective view of the same. The male member 300 includes a first cavity 310 for receiving the wire crimp device 205 and filament 220 combination (which is formed as discussed below with reference to FIG. 10-12). FIG. 8 shows a top view of the female member 400, and FIG. 7 shows a perspective view of the same. The female member 400 includes a first cavity 410 for receiving the wire crimp device 205 and filament 220 combination. When the male 300 and female 400 members are mated and pressed together, they preferably lock with each other through a 'snap fit.' Alternatively, the male and female members 300, 400 may be secured to one another through an adhesive disposed on one or both of the members, or through any other securing means known to those of ordinary skill in the art. Preferably, the wire crimp device 205 and filament 220 combination are disposed within the separate portions of the first cavities 310, 410 before the male 300 and female 400 members are mated, so that it is held tightly within the so-formed main body 230.

FIGS. 10-12 show additional details of the process for disposing the filament 220 within the main body 230 of the disposable tip 210. In particular, FIG. 10 shows the details for disposable tip 210' (discussed above with reference to FIG. 3), FIG. 11 shows the details for disposable tip 210'' (discussed above with reference to FIG. 4), and FIG. 12 shows the details for disposable tip 210''' (discussed above with reference to FIG. 6).

Figure 10A:
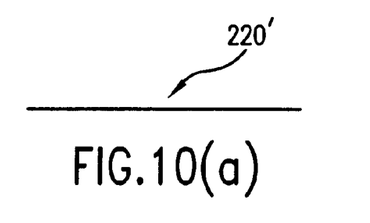
FIG. 10(a) shows a side view of a filament according to a first exemplary embodiment of the present invention.
Figure 10B:
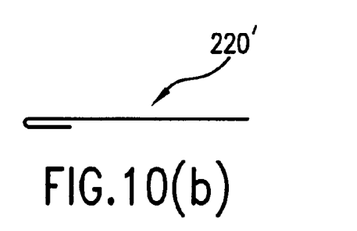
FIG. 10(b) shows a side view of the filament shown in FIG. 10(a) being bent in a "U" shape.
Figure 10C:
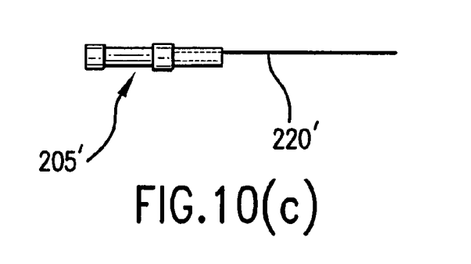
FIG. 10(c) shows a side view of the filament shown in FIG. 10(a) being bent inserted into a wire crimp device.
Figure 10D:
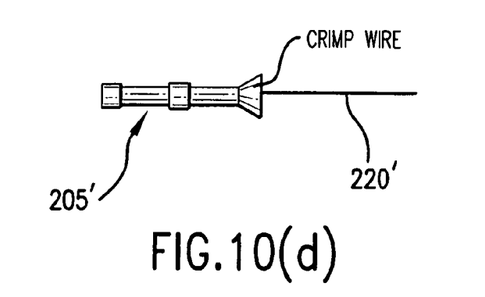
FIG. 10(d) shows a side view of the filament shown in FIG. 10(a) being crimped in the wire crimp device.
Figure 10E:
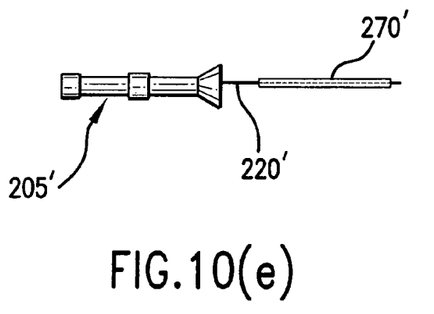
FIG. 10(e) shows a side view of the filament shown in FIG. 10(a) with an insulating sheath being applied.
Figure 10F:
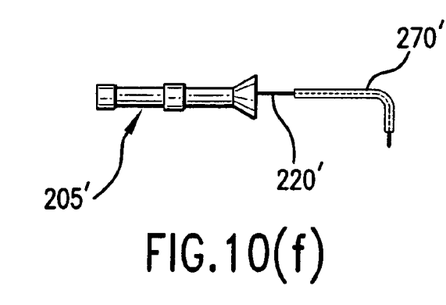
FIG. 10(f) shows a side view of the filament shown in FIG. 10(a) being bent at an angle.

With reference to disposable tip 210', FIG. 10(a) shows the filament 220' in its original state, as a long piece of wire. FIG. 10(b) shows the filament 220' being partially bent to form a "U" shape. FIGS. 10(c) and 10(d) show the filament 220' being inserted in the wire crimp device 205' and being crimped. FIG. 10(e) shows the application of the sheath 270' to the end of the filament 220' which extends beyond the wire crimp device 205'. Finally, FIG. 10(f) shows the filament 220' being bent at an angle (e.g., 90) with respect to the main axis of the wire crimp device 205'. At this point, the wire crimp device 205' is ready to be inserted into the main body 230' of the disposable tip 210'.

Figure 11A:
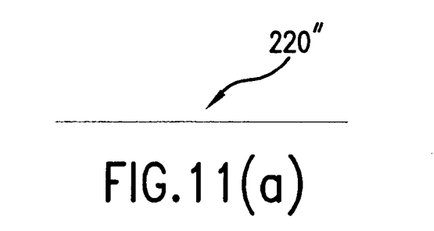
FIG. 11(a) shows a side view of a filament according to a second exemplary embodiment of the present invention.
Figure 11B:
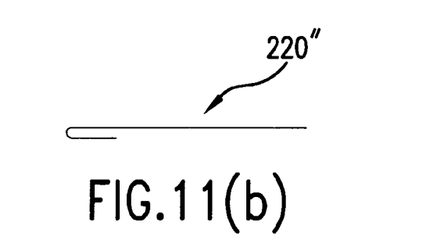
FIG. 11(b) shows a side view of the filament shown in FIG. 11(a) being bent in a "U" shape.
Figure 11C:
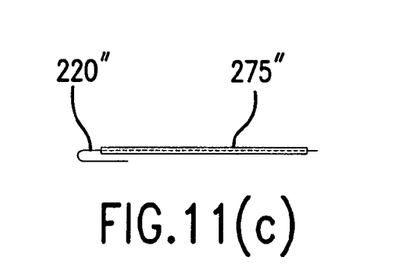
FIG. 11(c) shows a side view of the filament shown in FIG. 11(a) with an internal insulating sheath being applied.
Figure 11D:
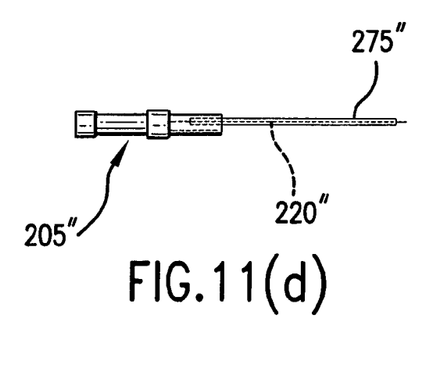
FIG. 11(d) shows a side view of the filament shown in FIG. 11(a) being bent inserted into a wire crimp device.
Figure 11E:
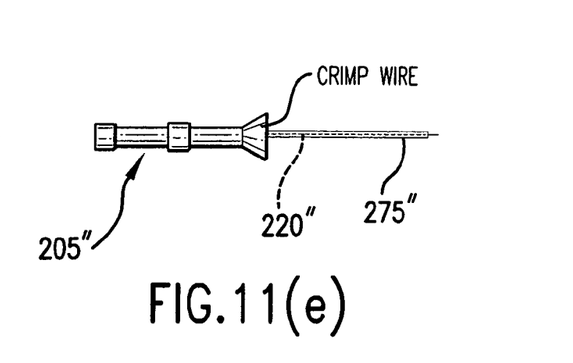
FIG. 11(e) shows a side view of the filament shown in FIG. 11(a) being crimped in the wire crimp device.
Figure 11F:
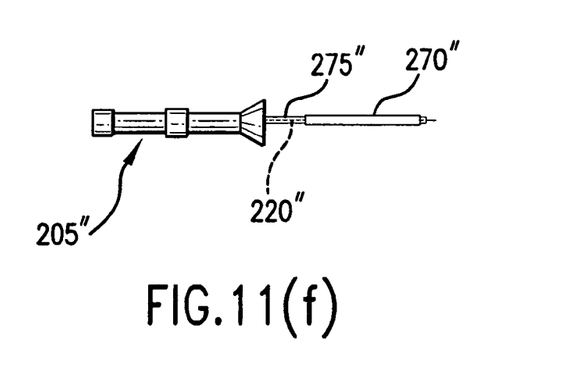
FIG. 11(f) shows a side view of the filament shown in FIG. 11(a) with an insulating sheath being applied.
Figure 11G:
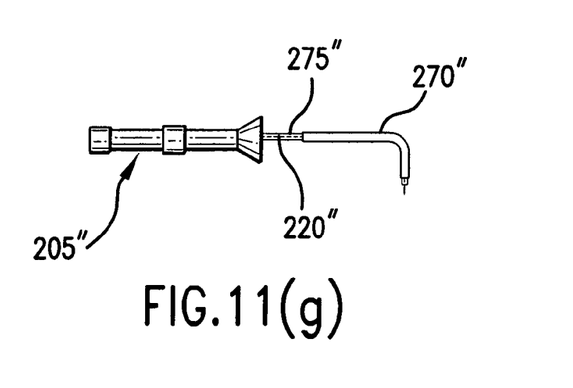
FIG. 11(g) shows a side view of the filament shown in FIG. 11(a) being bent at an angle.

With reference to disposable tip 210", FIG. 11(a) shows the filament 220" in its original state, as a long piece of wire. FIG. 11(b) shows the filament 220" being partially bent to form a "U" shape. FIG. 11(c) shows the application of an internal sheath 275". FIGS. 11(d) and 11(e) show the filament 220" (with internal sheath 275") being inserted in the wire crimp device 205" and being crimped. FIG. 11(f) shows the application of the (external) sheath 270" to the end of the filament 220" which extends beyond the wire crimp device 205". Finally, FIG. 11(g) shows the filament 220" being bent at an angle (e.g., 90) with respect to the main axis of the wire crimp device 205". At this point, the wire crimp device 205" is ready to be inserted into the main body 230" of the disposable tip 210".

Figure 12A:
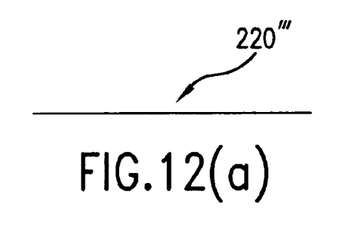
FIG. 12(a) shows a side view of a filament according to a third exemplary embodiment of the present invention.
Figure 12B:
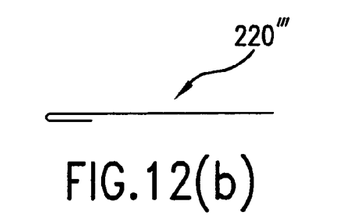
FIG. 12(b) shows a side view of the filament shown in FIG. 12(a) being bent in a "U" shape.
Figure 12C:
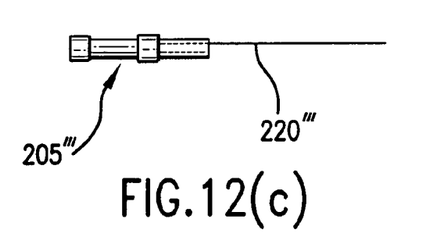
FIG. 12(c) shows a side view of the filament shown in FIG. 12(a) being bent inserted into a wire crimp device.
Figure 12D:
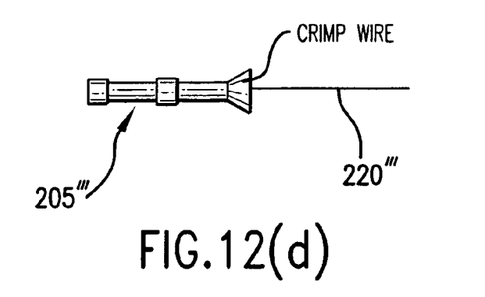
FIG. 12(d) shows a side view of the filament shown in FIG. 12(a) being crimped in the wire crimp device.
Figure 12E:
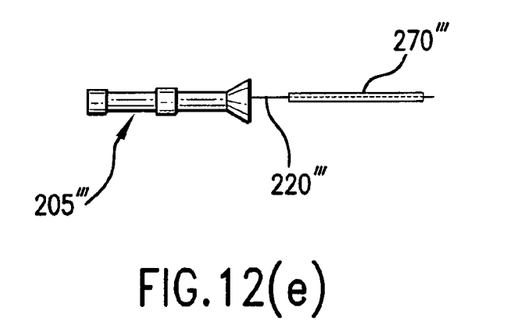
FIG. 12(e) shows a side view of the filament shown in FIG. 12(a) with an insulating sheath being applied.
Figure 12F:
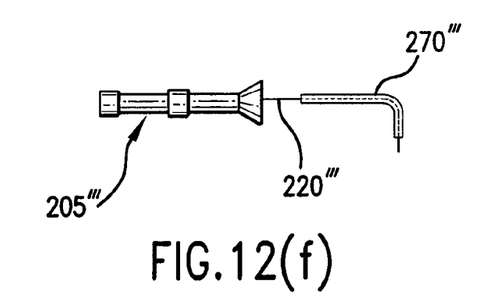
FIG. 12(f) shows a side view of the filament shown in FIG. 12(a) being bent at an angle.

With reference to disposable tip 210''', FIG. 12(a) shows the filament 220''' in its original state, as a long piece of wire. FIG. 12(b) shows the filament 220''' being partially bent to form a "U" shape. FIGS. 12(c) and 12(d) show the filament 220''' being inserted in the wire crimp device 205''' and being crimped. FIG. 12(e) shows the application of the sheath 270''' to the end of the filament 220''' which extends beyond the wire crimp device 205'''. Finally, FIG. 12(f) shows the filament 220''' being bent at an angle (e.g., 90) with respect to the main axis of the wire crimp device 205'''. At this point, the wire crimp device 205''' is ready to be inserted into the main body 230''' of the disposable tip 210'''.

The plasma incising system 100 may be utilized to perform surgical procedures, such as for example, a sclerostomy procedure or a corneal scleral ostomy procedures (i.e., glaucoma procedures). In one type of glaucoma surgery, the plasma incising system 100 (particularly the disposable tip 210) is first used to create an ostomy through the sclera. The disposable tip 210 is then used to create a transchoroidal ostomy in the center of the previously created scleral pit. The foot pedal 120 should be engaged only when the disposable tip 210 is actively used to incise tissue. When the foot pedal 120 is activated, the disposable tip 210 cuts with a controlled electromagnetic field. Disposable tip 210 should not be re-used or re-sterilized for a second or subsequent surgical case. The filament 220 of the disposable tip 210 is bent at an optimal predetermined angle. Further bending or manipulation of the filament 220 angle may reduce the cutting precision of the disposable tip 210.

The operation of the plasma incising system 100 will next be described. First, the user should assure that the rechargeable batteries are sufficiently charged. This can be accomplished by depressing the ON-OFF Switch and checking to see that the "LOW BAT" Indicator Light does not illuminate. If the "LOW BAT" Indicator Light illuminates, the rechargeable batteries inside the plasma generating unit 105 will require recharging. As noted above, the plasma generating unit 105 can only be recharged with the "ON-OFF" Switch is in the "OFF" position. The plasma generating unit 105 may be recharged by connecting the AC Battery Charger cable the electrical connector labeled "CHARGER" on the back panel 107 of the plasma generating unit 105, and connecting the other end to a standard 120/240 VAC, 50/60 Hz outlet. Once the AC Battery Charger is connected the user should ensure that the "CHARGING" Indicator Light on the front panel 106 of the plasma generating unit 105 is illuminated.

If the batteries of the plasma generating unit 105 are sufficiently charged, the user may begin operation by sterilizing the plasma wand 110. The plasma wand 110 may be sterilized by heat autoclave with a four (4) minute sterilization at 270 Fahrenheit (F), prior to each surgical procedure. After the plasma wand 110 has been sterilized, the user should connect the plasma wand to the plasma generating unit 105. Then the user should connect the foot pedal 120 to the plasma generating unit 105. Once the plasma wand 110 and foot pedal are connected to the plasma generating unit 105, the user may insert a disposable tip 210 into the plasma wand. To install the disposable tip 210, the user should align the first (open) end of . . . .

Once the disposable tip 210 is inserted in the plasma wand 110 the user may activate the ON-OFF Switch (i.e., toggle it to the "ON" position). At this point, the user may adjust the power of the plasma generating unit 105 by utilizing the "CUT POWER" and "CUT INTENSITY" dials described above. In most instances, the user should begin with the "CUT POWER" dial set to "MEDIUM" and the "CUT INTENSITY" dial set to level "5". The various "CUT POWER" settings of "low," "medium" and "high" provide means for increasing a power burst duration, which results in an increase in the duration of the electromagnetic field around the cutting filament 220. The "CUT INTENSITY" settings may be progressively increased from "1" to "10," and such increases results in a progressive increase in voltage levels at the cutting filament 220. In sum, increasing either the "CUT POWER" or "CUT INTENSITY" will result in a larger and deeper cut.

With particular reference to the transscleral portion of a sclerostomy (i.e., open angle glaucoma) procedure, the following guidelines should be observed for the "CUT POWER" and "CUT INTENSITY" settings. When treating an eye with a sclera of normal thickness, the user should begin by setting the "CUT POWER" at "medium" and the "CUT INTENSITY" at "5". As the sclera becomes thickened, such as in nanophthalmus, or measured by peripheral corneal pachymetry of greater than nine hundred (900) microns, "CUT POWER" and "CUT INTENSITY" should slowly be increased. Ablation should be increased by increasing the intensity by two (2) intensity units per attempted application. If the disposable tip 210 fails to ablate satisfactorily upon application, then the ablation should be stopped and raised by two (2) intensity units. The "CUT POWER" should be set to "high" if a cut power of "medium" and cut intensity of "9" proves clinically unsatisfactory. If higher power is needed, then the unit should be switched to high power with the intensity setting at "5". If needed, the intensity may be raised in a manner as described above. If the eye wall is clinically judged "thin" such as with bluish/purplish discoloration of sclera, then the initial power setting should be lowered. Thinned sclera is often seen with severe autoimmune disease. If the sclera is judged severely thin, then the initial settings should be "low" and "1". If the sclera is judged moderately thin by clinical means, then the initial settings should be "low" and "3". If the sclera is judged mildly thin, then the initial settings should be "low" and "5".

With particular reference to the transciliary portion of the sclerostomy procedure, the following guidelines should be observed for the "CUT POWER" and "CUT INTENSITY" settings. For transciliary ablation, the plasma generating unit 105 should be set to a "CUT POWER" of "medium" and a "CUT INTENSITY" of "5."

The specifics of using the system 100 to perform a sclerostomy procedure will now be described. First the user (i.e., surgeon) should examine the eye and the target surgical site.

The user should establish a desired sclerostomy site. A five (5) millimeter (mm) fornix based conjunctival flap is then raised and centered over the sclerostomy site. Once the conjunctival flap is raised, hemostasis is achieved by employing as little cautery as possible. An incision with the plasma wand 110 causes hemostasis in the path of incision. It is recommended that minimal standard cautery is employed such that minimal iatrogenic damage/trauma is produced on tissue in the operative field.

Once the above-described hemostasis is achieved, the system 100 may be used to make the transscleral incision. First, a 'transscleral' disposable tip 210' is mounted on the plasma wand 110 (i.e., a disposable tip according to certain characteristics set for transscleral incisions; see description above). The end of the 'transscleral' disposable tip 210' is used to ablate through the sclera, while the tip is held perpendicular to the sclera. The scleral ablation pit should have a nominal diameter of 0.6 mm. However, the actual size of the ablation pit is increased as one raises the "CUT INTENSITY" and the "CUT POWER" settings. The ablation through sclera is stopped when the sclera at the base of the pit manifests a darkened brownish discoloration which indicates the interface of the ciliary body. The ablation pit is preferably placed behind the iris root as identified by transillumination of the anterior chamber of the eye. The disposable transscleral incising tip 210' is then removed from the plasma wand 110 and discarded.

Next, a 'transciliary' disposable tip 210" (or 210'") is mounted on the plasma wand 110 (i.e., a disposable tip according to certain characteristics set for transciliary incisions; see description above). The 'transciliary' disposable tip is then used to ablate a nominal ostomy from a one hundred fifty (150) to six hundred (600) micron pore in the center of the previously created scleral pit. The actual size of the ciliary pore is increased by increasing the "CUT INTENSITY" and the "CUT POWER" settings, as discussed above. Ablation of sclera and of ciliary body must be performed with the user depressing the foot pedal 120 of the system 100, and thereby activating the plasma generating unit 105. The transciliary pore is completed when aqueous fluid is seen to seep out of the incision pore site. If an initial ablation through ciliary body is performed but no aqueous is seen to seep from the pore, then the pore is not patent. In this case, the user should ablate deeper in the same pore site that was initially created in the ciliary body. Once sufficient aqueous fluid is observed seeping from the surgical site, the ablation is complete. However, is an inadequate aqueous flow is created as judged clinically, then the transciliary tip should be passed in and out of the ostomy into the posterior chamber of the eye. In this fashion, debris is removed from the ostomy and/or the ostomy may be enlarged. Furthermore, strands of ocular vitreous gel may be blocking or plugging the internal side of the ostomy whereupon repeated passage of the activated ablation tip into this unwanted vitreous gel in the posterior chamber of the eye causes an ablation (and removal) of the unwanted vitreous gel by producing a localized plasma ablative vitrectomy in the area of the ostomy. In this way, encumberance to healthy aqueous flow out of the eye is removed. If blood oozes from the surgical site, a weck cell sponge should be placed over the surgical site to tamponade the bleeding. The pressure should be applied for 3-4 minutes before removing the surgical sponge. If there is residual bleeding, the above tamponade procedure should be repeated. When the transciliary procedure is complete, the disposable transciliary tip 210" should be removed from the plasma wand 110 and discarded.

Next, the conjunctival flap should be sutured back into its natural position with one or two interrupted 10-0 nylon sutures (or surgeon preference). Classically, a water tight closure has been recommended by many authors even preferring a limbus based flap. This may be obtained by close interrupted sutures or a locking running suture. Steroid and antibiotic may also be injected subconjunctivally 180° away from the pore site. The eye should also be thoroughly examined for appropriate surgical integrity, and then patched with a sterile ophthalmic bandage. The patch should be removed, and the eye given a thorough examination within twenty-four (24) hours of the procedure.

In one exemplary embodiment of the present invention, the plasma generating unit 105 includes the following characteristics:

Frequency: 9.8 MHz (All Modes)
Output Power: Variable from 1.25 Watts to 3.50 Watts
Setting 1 Average Output Power 1.25 Watts
Setting 5 Average Output Power 2.38 Watts
Setting 10 Average Output Power 3.50 Watts
Output Voltage: Variable from 180 Peak Volts to 230 Peak Volts
Setting 1 Average Output Voltage 180 Vp-p
Setting 5 Average Output Voltage 205 Vp-p
Setting 10 Average Output Voltage 230 Vp-p Although exemplary embodiments of disposable tips 210 have been described above for use in transscleral and transciliary procedures (i.e., 210', 210", 210'"), those of ordinary skill in the art will realize that these disposable tips may be used for other types of operations. Those of ordinary skill in the art will also realize that by varying the dimensions of the various elements that comprise the disposable tip 210 (e.g., filament length within the main body, filament length outside the sheath, filament diameter, sheath size, sheath material, number of sheathes, etc.), varied disposable tips for varied operations may be created, and those types of tips are considered within the scope of the present invention.

Although the invention has been described in terms of exemplary embodiments, it is not limited thereto. Rather, the appended claims should be construed broadly to include other variants and embodiments of the invention which may be made by those skilled in the art without departing from the scope and range of equivalents of the invention.

What is claimed is:

1. A disposable tip for use with a plasma surgical device comprising:
   a main body having a longitudinal axis therethrough and a proximal and distal end;
   a wire crimp device;
   a filament comprised of an electrically conductive wire and an insulating sheath;
   wherein the proximal end of the main body includes a first recess for receiving an electrical connector disposed within a plasma wand;
   wherein the insulating sheath partially encloses the electrically conductive wire;
   wherein the filament extends from said distal end of said main body;
   wherein the main body is comprised of a male member and a female member, each having a second recess to receive the wire crimp device and the filament, and each having a contact portion along an outer edge parallel to the longitudinal axis;
   wherein the male member and the female member interlock in a snap fit with one another along respective contact portions; and
   wherein when the wire crimp device is received in the cavity and the male and female members interlock with one another, an electrical connection is made between a plasma wand electrical connector, the wire crimp device, and the electrically conductive filament.

2. The disposable tip of claim 1, wherein a first portion of the electrically conductive wire is disposed within the insulating sheath, and a second portion of the electrically conductive wire extends outside the insulating sheath.

3. The disposable tip of claim 2, wherein the second portion of the electrically conductive wire is approximately 0.1 to 1.5 millimeters long.

4. The disposable tip of claim 1, wherein the main body distal end comprises a frustroconical end and the main body proximal end comprises a second cylindrical end, wherein the filament extends from the frustoconcial end of the main body.

5. The disposable tip of claim 1, wherein a first portion of the filament is disposed at a predetermined angle with respect to the main body longitudinal axis.

6. The disposable tip of claim 5, wherein the first portion of the filament is disposed at a 90 degree angle with respect to the main body longitudinal axis.

* * * * *